United States Patent
Liu et al.

(10) Patent No.: US 10,215,702 B2
(45) Date of Patent: Feb. 26, 2019

(54) METHOD FOR PREPARING A SURFACE ENHANCED RAMAN SPECTROSCOPY PARTICLE

(75) Inventors: Shuhua Liu, Singapore (SG); Kwok Wei Shah, Singapore (SG); Michelle Low, Singapore (SG); Zhi Wei Seh, Singapore (SG); Ming-Yong Han, Singapore (SG); Kaustabh Kumar Maiti, Singapore (SG); Kiat Seng Jason Soh, Singapore (SG); Dinish Unnimadhava Kurup Soudamini Amma, Singapore (SG); Malini Olivo, Singapore (SG); Young-Tae Chang, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 951 days.

(21) Appl. No.: 13/562,104

(22) Filed: Jul. 30, 2012

(65) Prior Publication Data
US 2013/0196057 A1 Aug. 1, 2013

(30) Foreign Application Priority Data

Jul. 28, 2011 (SG) .............................. 201105454-1

(51) Int. Cl.
*G01N 21/65* (2006.01)
(52) U.S. Cl.
CPC ........... *G01N 21/65* (2013.01); *G01N 21/658* (2013.01)
(58) Field of Classification Search
CPC ....... G01N 21/65; G01N 21/658; B82Y 30/00

USPC .................................................. 427/212–222
See application file for complete search history.

(56) References Cited

U.S. PATENT DOCUMENTS

| 7,982,870 B2 | 7/2011 | Lee et al. |
|---|---|---|
| 2003/0166297 A1* | 9/2003 | Natan ........................... 436/166 |
| 2009/0140206 A1* | 6/2009 | Nie et al. ................. 252/301.16 |
| 2011/0197787 A1* | 8/2011 | Kawai et al. .............. 106/287.1 |

FOREIGN PATENT DOCUMENTS

| WO | WO-2005062741 | 7/2005 |
|---|---|---|
| WO | WO-2009102598 | 8/2009 |
| WO | WO 2010/121064 | * 10/2010 |

OTHER PUBLICATIONS

Chang, Chia-Lu, et al., "Kinetics of Silica Particle Formation in Nonionic W/O Microemulsions from TEOS", AIChE Journal, vol. 42, No. 11, (Nov. 1996), 3153-3163.
Chen, Min, et al., "Preparation of Silica-Coated Polystyrene Hybrid Spherical Colloids", Macromolecular Chemistry and Physics, vol. 206, (2005), 1896-1902.
Liu, Shuhua, et al., "Silica-Coated Metal Nanoparticles", Chemistry: An Asian Journal, vol. 5, (2010), 36-45.
(Continued)

*Primary Examiner* — Elizabeth A Burkhart
(74) *Attorney, Agent, or Firm* — Womble Bond Dickinson (US) LLP

(57) ABSTRACT

There is provided a method of preparing a surface enhanced Raman spectroscopy (SERS) particle comprising the step of encapsulating a plurality of Raman molecules on the surface of a metallic core with a biocompatible protective shell at an elevated temperature selected to decrease the encapsulation time by more than one-fold relative to an encapsulation performed at 20° C.

20 Claims, 7 Drawing Sheets

(56) References Cited

OTHER PUBLICATIONS

Liu, Shuhua, et al., "Surface-functionalized silica-coated gold nanoparticles and their bioapplications", *Talanta*, vol. 67, (2005), 456-461.

Liu, Shuhua, et al., "Synthesis, Functionalization and Bioconjugation of Monodisperse, Silica-Coated Gold Nanoparticles: Robust Bioprobes", *Advanced Functional Materials*, vol. 5, (2005), 961-967.

Liz-Marzan, Luis M., et al., "Synthesis of Nanosized Gold-Silica Core-Shell Particles", *Langmuir*, vol. 12, (1996), 4329-4355.

* cited by examiner

METHOD FOR PREPARING A SURFACE ENHANCED RAMAN SPECTROSCOPY PARTICLE

This application claims priority to Singapore Patent Application Number 201105454-1, filed Jul. 28, 2011, which is hereby incorporated by reference for all purposes.

TECHNICAL FIELD

The present invention generally relates to a method for preparing a surface enhanced Raman spectroscopy (SERS) particle. The present invention also relates to a particle as prepared herein.

BACKGROUND

In recent years, metallic nanostructures have been extensively studied in the context of their optical properties.

One of the main reasons for the interest in the interaction of metallic nanostructures with light is the plasmonic property of such nanostructures in and near the visible frequency spectrum.

Plasmons are the coupled oscillations of light and free electrons at the metal-dielectric interface. These coupled oscillations result in optical fields that can be used for the propagation and localization of light beyond the diffraction limit. Among the various optical spectroscopy techniques available, Surface-Enhanced Raman Scattering (SERS) has been shown to have important applications for single-molecule sensitivity and chemical specificity.

A range of plasmonic nanostructures of different architectures have been developed in attempts to exploit their capabilities in SERS, including nano-spheres, cubes, triangles, pyramids, rods, wires and tips.

The main challenge in the use of such nanostructures is attempting to create SERS hot-spots, where the Raman scattering signal may be maximized.

Commonly, the noble metals of gold, silver or copper have been investigated for their ability to enhance the Raman scattering signal. In same instances, bimetallic materials (e.g., of gold and silver) have been studied. Various other composites utilizing a mix of silica and other noble metals have also been explored.

Fundamentally the spherical silica nanocomposite has generated keen interest in the field of biomaterials. In general, such particles may be synthesized by the addition of silicon alkoxide to a reverse water-in-oil microemulsion. The diffusion of the alkoxide into the water droplets results in the hydrolysis of the alkoxide and subsequently the formation of a oxy-hydroxy-silicate species and alcohol. A complicating factor in the use of this method is that certain bio-applications of such a nanostructure are stable over only a limited range of pH values; this may not correspond to the optimum pH for the required rapid hydrolysis and condensation reactions of the selected alkoxide.

In addition, in silica-based composites, an optimal thickness is often sought for the silica-shell layer. For example, if the silica coating within a composite SERS material is relatively thin, particularly in the presence of an alcohol solvent, the dissolution/desorption of pre-adsorbed Raman molecules at certain conditions may occur, leading to a potentially drastic decrease in the intensity of the SERS signal. Often, the Stöber process is used for the purpose of thickening the silica shell via the adoption of a tedious three-step method: (1) surface activation for silanization with coupling silane agents (2) initial silica deposition with sodium silicate in an aqueous solution and (3) extensive growth of the silica shell with a silicon alkoxide tetraethyl-orthosilicate) in an alcohol solution. Among the three steps mentioned, the second one is generally not well-controlled and takes a length of time (from 24 h to weeks depending on the targeted thickness) before a silica shell becomes thick enough to stabilize the particles in alcohol for the subsequent and extensive growth of silica.

There is a need to provide method for preparing a SERS particle that overcomes, or at least ameliorates, one or more of the disadvantages described above.

SUMMARY

According to a first aspect, there is provided a method of preparing a surface enhanced Raman spectroscopy (SERS) particle comprising the step of encapsulating a plurality of Raman molecules on the surface of a metallic core with a biocompatible protective shell at an elevated temperature selected to decrease the encapsulation time more than one-fold relative to an encapsulation performed at 20° C.

Advantageously, the disclosed process, due to the use of an encapsulation temperature of at least 30° C., may result in the encapsulation of the Raman molecules by the biocompatible protective shell in a shorter period of time compared to a process which was carried out at room temperature, which is typically carried out at a temperature of about 20° C. to about 25° C. Advantageously, this may aid in substantially preventing the dissociation of the Raman molecules from the particle.

Even more advantageously, the use of the higher encapsulation temperature may result in a particle with an enhanced SERS intensity as compared to another particle having a shell of the same thickness but when made at room temperature.

The process may further comprise the step of increasing the thickness of the shell. The increasing step may comprise the step of adding an aqueous solution of a coating precursor under alkaline conditions.

Advantageously, the use of an aqueous solution during the increasing step may result in a particle with enhanced SERS intensity as compared to a prior art process which uses an alcoholic solution to obtain the shell on the particle. Accordingly, the increasing step may optionally exclude the use of an alcohol.

According to a second aspect, there is provided a particle prepared from the method of any one of claims 1 to 20 comprising a metallic core having a plurality of Raman molecules extending from the surface of the metallic core and a biocompatible protective shell encapsulating the Raman molecules.

DEFINITIONS

The following words and terms used herein shall have the meaning indicated:

The term "nanoparticle", as used herein relates to the average dimension of a nanoparticle having a size of less than about 1000 nm, particularly less than about 500 nm, more particularly less than about 100 nm. The average dimension may be between about 10 nm to about 100 nm. The nanoparticles may not be exactly spherical and the dimension of the nanoparticle may refer to the equivalent diameter of the nanoparticles relative to a spherical nanoparticle.

The term "microparticle", as used herein relates to the average dimension of a microparticle having a size of less than about 1000 µm, particularly less than about 500 µm, more particularly less than about 100 µm. The average dimension may be between about 10 µm to about 100 µm. The microparticles may not be exactly spherical and the dimension of the microparticle may refer to the equivalent diameter of the microparticles relative to a spherical microparticle.

The phrase "more than one-fold" when referring to a decrease in the encapsulation time as compared to a reference encapsulation time means the multiplication of the reference encapsulation time by 1/x, in which x is a number more than 1, to obtain the encapsulation time at the elevated temperature.

The phrase "at, least two-fold" when referring to a decrease in the encapsulation time as compared to a reference encapsulation time means the multiplication of the reference encapsulation time by ½ to obtain the encapsulation time at the elevated temperature. Hence, the phrase "at least n-fold" means the multiplication of the reference encapsulation time by 1/n to obtain the encapsulation time at the elevated temperature.

The term "protective" as used herein when referring to the shell, refers to the ability of the shell to shield the Raman molecules extending from the core from damage or exposure to an external environment.

The term "biocompatible" as used herein when referring to the shell, means that the shell is non-immunogenic, non-allergenic and non-toxic when administered in vivo. As such, the shell does not alter the biological functions of a living organism.

The term "elevated temperature" refers to a temperature that is higher than a reference temperature set at 20° C. Fence, the elevated temperature means any temperature that is more than 20° C., or at least 30° C.

The term "silica" as used herein when referring to the shell, refers to an oxide of silicon having the approximate chemical formula $SiO_2$, without regard to water or hydroxyl content.

The phrase "substantially free of an alcohol" may not include the use of an alcohol in a particular reaction solution or process step, wherein the alcohol is defined by the general formula $C_nH_{2n+1}OH$. In the event that an alcohol is present in the reaction solution or process step due to contamination of the reactant(s) or reaction solution, the amount of alcohol should be less than about 0.5 wt %, less than about 0.1 wt %, or less than about 0.01 wt %.

The term "Raman molecule," as used herein, is to be interpreted to refer to any substance which produces a detectable Raman spectrum, which is distinguishable from the Raman spectra of other components present, when illuminated with a radiation at an excitation wavelength.

The term "Surface-Enhanced Raman Scattering" or "SERS" as used herein, is to be interpreted to refer to the increase in Raman scattering exhibited by certain molecules in proximity to certain metal surfaces.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2 of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary non-limiting embodiments of a method of preparing a SERS particle will now be disclosed.

The method comprises the step of encapsulating a plurality of Raman molecules on the surface of a metallic core with a biocompatible protective shell at an elevated temperature selected to decrease the encapsulation time more than one-fold relative to an encapsulation performed at 20° C.

Due to the use of the elevated temperature, the encapsulation time may be decreased at least two-fold, at least three-fold, at least four-fold, at least five-fold, at least six-fold, at least seven-fold, at least eight-fold, at least nine-fold, at least ten-fold, at least eleven-fold or at least twelve-fold, relative to an encapsulation performed at 20° C.

The encapsulation time at the elevated temperature may be at least about 10% of the encapsulation time when the temperature is 20° C. The encapsulation time may be selected from about 10% to about 90%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 10% to about 75%, about 10% to about 80%, about 10% to about 85%, about 15% to about 90%, about 20% to about 90%, about 25% to about 90%, about 30% to about 90%, about 35% to about 90%, about 40% to about 90%, about 45% to about 90%, about 50% to about 90%, about 55% to about 90%, about 60% to about 90%, about 65% to about 90%, about 70% to about 90%, about 75% to about 90%, about 80% to about 90% and about 85% to about 90%, as compared to an encapsulation time at a temperature of 20° C. The encapsulation time at the elevated temperature may be about 15% of the encapsulation time at a temperature of 20° C.

The elevated temperature may be selected from the group consisting of 30° C. to 95° C., 30° C. to 40° C., 30° C. to 50°

C., 30° C. to 60° C., 30° C. to 70° C., 30° C. to 80° C., 30° C. to 90° C., 40° C. to 95° C., 50° C. to 95° C., 60° C. to 95° C., 70° C. to 95° C., 80° C. to 95° C. and 90° C. to 95° C. The elevated temperature may be about 70° C. If the elevated temperature is about 70° C., the encapsulation time may be about 8 hours.

The time period for the encapsulating step at the elevated temperature may be selected from the group consisting of from about 4 hours to about 45 hours, about 4 hours to about 40 hours, about 4 hours to about 35 hours, about 4 hours to about 30 hours, about 4 hours to lout 25 hours, out 4 hours to about 20 hours, about 4 hours to about 15 hours, about 4 hours to about 10 hours, about 4 hours to about 5 hours, about 5 hours to about 45 hours, about 10 hours to about 45 hours, about 15 hours to about 45 hours, about 20 hours to about 45 hours, about 25 hours to about 45 hours, about 30 hours to about 45 hours, about 35 hours to about 45 hours and about 40 hours to about 45 hours. The encapsulation time may be about 8 hours. Hence, if the reference encapsulation time is about 48 hours, the encapsulation time of 4 hours is a 12-fold decrease, the encapsulation time of 8 hours is a 6-fold decrease while the encapsulation time of 45 hours is a 1.07-fold decrease.

The process may comprise the step of adding the metallic core to a solution comprising the Raman molecules, an organo coupling agent and a silica precursor under conditions to cause the Raman molecules to extend from the surface of the metallic core.

The biocompatible protective shell may comprise silica. The silica shell may function to encapsulate and protect the Raman molecules. The silica shell may be highly biocompatible and may be suitable for biomedical applications such as in vivo applications. The silica shell may be amendable for further functionalization with desired biomolecules such as antibodies), which again allows for biomedical applications.

The organo coupling agent may comprise amino (—$NH_2$) functional groups and hydroxyl (—OH) functional groups. The organo coupling agent may undergo a hydrolysis reaction in order to form the hydroxyl functional groups. The amino functional groups may bind with the surface of the metallic core to result in a molecular monolayer of the organo coupling agent on the surface of the metallic core. This may result in the extension of the hydroxyl functional groups outwards and away from the metallic core to facilitate the adsorption of the Raman molecules on the surface of the metallic core and cross-link with the silica precursor to undergo further hydrolysis and condensation to form the silica shell. Hence, the adsorption and encapsulation of the Raman molecules may occur almost simultaneously.

Due to the use of the elevated temperature as mentioned above, the inventors hate surprisingly found that this elevated temperature may aid in substantially enhancing the reaction rate so as to increase the hydrolysis and condensation of Si—OH to form the Si—O—Si network. Accordingly, due to the faster formation of the silica shell at the elevated temperature, encapsulation of the Raman molecules by the shell can also occur at a faster rate, hence substantially minimizing dissociation of the Raman molecules from the particle.

The metallic core, Raman molecules, organo coupling agent and silica precursor may be subjected to shaking so as to allow the formation of the molecular monolayer of the organo coupling agent around the metallic core.

The metallic core may comprise a transition metal. The transition metal may be selected from the group consisting of silver, gold, platinum and copper.

The Raman molecule may not be particularly limited and can include Raman molecules over a broad wavelength from the visible- to near infrared with either specific functional groups (including —SH, —$NH_2$, —COOH, etc) or with positively (or negatively) charged surfaces. The Raman molecules may be heterocyclic Raman molecules. The Raman molecule may be selected from the group consisting of a near infrared (NIR)-SERS active organic dye which belongs to the tricarbocyanine library (CyNAMLA), 4-(4-Aminophenylazo)phenylarsonic acid monosodium salt, arsenazo I, basic fuchsin, Chicago sky blue, direct red 81, disperse orange 3, HABA (2-(4-hydroxyphenylazo)-benzoic acid), erythrosin B, trepan blue, ponceau S, ponceau SS, 3,3'-diethylthiatricarbocyanine, 1,5-difluoro-2,4-dinitrobenzene, cresyl violet, 2-naphthalenethiol, crystal violet, pyrazole, p-dimethylaminoazobenzene and mixtures thereof. The Raman molecule may be a fluorescent dye. The Raman molecules may be chosen based on the application of the SERS particle. For example, it deeper skin tissue penetration (about 15 to 25 nm) is required, the Raman molecule may be of the Cynam library. The Raman molecule may be CyN-AMLA-381.

The Raman molecules may be adsorbed on the surface of the metallic core or may be covalently bonded to the surface.

The organo coupling agent may be an organo-silane coupling agent. The organo-silane coupling agent may be selected from the group consisting of epoxysilane, mercaptosilane, alkylsilane, phenylsilane, ureidosilane and vinylsilane, titanium based compounds, aluminum chelates, and aluminum/zirconium based compounds.

Exemplary organo-silane coupling agents are not limited and can include silane coupling agents such as 3 aminopropyltriethoxysilane, 4-aminobutyltriethoxysilane, 3-aminopropyltris(methoxyethoxyethoxy)silane, 11-aminoundecyltriethoxysilane, N-(2-aminoethyl)-3-aminopropyltrimethoxysilane, N-(2-aminoethyl)-3-aminopropyltriethoxysilane, N-(6-aminohexyl) aminomethyltriethoxysilane, N-(6-aminohexyl) aminomethyltrimethoxysilane, N-(2-aminoethyl)-11-aminoundecyltrimethoxysilane, etc. These may be used alone or in combination of two or more thereof.

In one embodiment, the organo-silane coupling agent is an organosilane compound having the formula (Y—R)$_n$Si$X_m$, where Y is an amino functional group, R is a $C_{3-6}$-alkyl group, X is a $C_{1-6}$-alkoxy group, and n and m are integers such that the sum of n and m is 4 (n+m=4). Accordingly, the coupling agent may be aminopropyltrimethoxysilane (APTMS) having the formula (I) below:

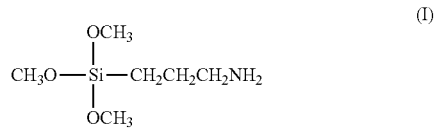

(I)

In another embodiment, the organosilane coupling agent may be 3-glycidoxypropyltrimethoxysilane.

The silica precursor may be a silicate. The silicate may be selected from the group consisting of sodium silicate, potassium silicate, lithium silicate, calcium silicate and magnesium silicate.

The concentration of the silica precursor (based on the water composition in the silica precursor solution) may be selected from the range of about 0.05 wt % to about 0.6 wt %, about 0.09 wt % to about 0.54 wt %, about 0.1 wt % to about 0.6 wt %, about 0.2 wt % to about 0.6 wt %, about 0.3 wt % to about 0.6 wt %, about 0.4 wt % to about 0.6 wt %, about 0.5 wt % to about 0.6 wt %, about 0.05 wt % to about 0.09 wt %, about 0.5 wt % to about 0.1 wt %, about 0.05 wt % to about 0.2 wt %, about 0.05 wt % to about 0.3 wt %, about 0.05 wt % to about 0.4 wt % and about 0.5 wt % to about 0.5 wt %.

The volume ratio of the silica precursor to the organo coupling agent may be about 45-55:1. The volume ratio of the Raman molecules to the organo coupling agent may be about 20-30:1. Hence, the volume ratio of the organo coupling agent:silica precursor: Raman molecules may be about 1:745-55:20-30.

The metallic or may have a cross-sectional diameter that is selected to achieve SERF. The cross-sectional diameter may be selected from about 50 nm to about 1000 nm, about 50 nm to about 100 nm, about 50 nm to about 150 nm, about 50 nm to about 200 nm, about 50 nm to about 250 nm, about 50 nm to about 300 nm, about 50 nm to about 350 nm, about 50 nm to about 400 nm, about 50 nm to about 450 nm, about 50 nm to about 500 nm, about 50 nm to about 550 nm, about 50 nm to about 600 nm, about 50 nm to about 650 nm, about 50 nm to about 700 nm, about 50 nm to about 750 nm, about 50 nm to about 300 nm, about 50 nm to about 850 nm, about 60 nm to about 900 nm, about 50 nm to about 550 nm, about 100 nm to about 1000 nm, about 150 nm to about 1000 nm, about 200 nm to about 1000 nm, about 250 nm to about 1000 nm, about 300 nm to about 1000 nm, about 350 nm to about 1000 nm, about 400 nm to about 1000 nm, about 450 nm to about 1000 nm, about 500 nm to about 1000 nm, about 550 nm to about 1000 nm, about 600 nm to about 1000 nm, about 650 nm to about 1000 nm, about 700 nm to about 1000 nm, about 750 nm to about 1000 nm, about 800 nm to about 1000 nm, about 850 nm to about 1000 nm, shout 900 nm to about 1000 nm and about 950 nm to about 1000 nm.

The metallic core may be grown from a metallic seed. For example, where the metallic core is gold, the gold seed may be grown using a solution of $HAuCl_4$ and sodium citrate under boiling. The gold may be stabilized with the sodium citrate so as to allow the formation of a molecular monolayer of the organo coupling agent as explained above. It is to be appreciated that depending on the type of metallic core to be used, the method of growing or increasing the size of the metallic seed is know. Alternatively, the metallic core having a desired cross-sectional diameter may be obtained commercially.

The silica layer may have a thickness selected from about 2 nm to about 10 nm, about 2 nm to about 3 nm, about 2 nm to about 4 nm, about 2 nm to about 5 nm, about 2 nm to about 6 nm, about 2 nm to about 7 nm, about 2 nm to about 8 nm, about 2 nm to about 9 nm, about 3 nm to about 10 nm, about 4 nm to about 10 nm, about 5 nm to about 10 nm, about 6 nm to about 10 nm, about 7 nm to about 10 nm, about 8 nm to about 10 nm, about 9 nm to about 10 nm, about 3 nm to about 5 nm and about 4 nm to about 5 nm.

The process may further comprise the step of increasing the thickness of the silica layer. The increasing step may comprise the step of adding an aqueous solution of a coating precursor under alkaline conditions. The aqueous solution may further comprise a catalyst selected from the group consisting of ammonia, 2-aminoethanethiol, ethanolamine, 2-(dimethylamino)ethanethiol, 2-(ethylthio)ethylamine and propylamine.

The aqueous solution may be substantially free of an alcohol. Hence, the aqueous solution may be substantially free of an alcohol, which has a general formula $C_nH_{2n+1}OH$.

The coating precursor may be 3-mercaptopropyltrimethoxysilane or 3-mercaptopropyltriethoxysilane. In one embodiment, the silane compound may be 3-mercaptopropyltrimethoxysilane. In another embodiment, the silane compound may be 3-mercaptopropyl triethoxysilane.

The alkaline conditions may be selected from a pH in the range of about 7 to about 10, about 7 to about 8, about 7 to about 9, about 8 to about 10 and about 9 to about 10. A base may be introduced during the increasing step to create the alkaline conditions. The base may be sodium hydroxide or potassium hydroxide. Alternatively or additionally, the catalyst may function as a replacement or addition of the bases listed here. If a catalyst such as ammonia only is used as the base, the pH may be adjusted by using different amounts or concentrations of the ammonia. Other catalysts that can be used may be selected from the group consisting of 2-aminoethanethiol, ethanolamine, 2-(dimethylamino)ethanethiol, 2-(ethylthio)ethylamine and propylamine.

The increasing step may be undertaken for a period of time from at least two hours. The time period may be at least two hours, at least three hours, at least four hours, at least five hours, at least six hours, at least seven hours, at least eight tours, at least nine hours, at least ten hours, at least 11 hours or at least 12 hours. The time period may be dependent on the amount of silica precursor added since the thickening of the silica shell will stop once the silica precursor is consumed.

The thickness of the silica layer after the increasing step may be about 10 nm to about 1100 nm, about 10 nm to about 50 nm, about 10 nm to about 100 nm, about 10 nm to about 150 nm, about 10 nm to about 200 nm, about 10 nm to about 250 nm, about 10 nm to about 300 nm, about 10 nm to about 350 nm, about 10 nm to about 400 nm, about 10 nm to about 450 nm, about 10 nm to about 500 nm, about 10 nm to about 550 nm, about 10 nm to about 600 nm, about 10 nm to about 650 nm, about 10 nm to about 700 nm, about 10 nm to about 750 nm, about 10 nm to about 800 nm, about 10 nm to about 850 nm, about 10 nm to about 900 nm, about 10 nm to about 950 nm, about 10 nm to about 1000 nm, about 10 nm to about 1050 nm, about 50 nm to about 1100 nm, about 100 nm to about 1100 nm, about 150 nm to about 1100 nm, about 200 nm to about 1100 nm, about 250 nm to about 1100 nm, about 300 nm to about 1100 nm, about 350 nm to about 1100 nm, about 400 nm to about 1100 nm, about 450 nm to about 1100 nm, about 500 nm to about 1100 nm, about 550 nm to about 1100 nm, about 600 nm to about 1100 nm, about 650 nm to about 1100 nm, about 700 nm to about 1100 nm, about 750 nm to about 1100 nm, about 800 nm to about 1100 nm, about 850 nm to about 1100 nm, about 900 nm to about 1100 nm, about 950 nm to about 1100 nm, about 1000 nm to about 1100 nm and about 1050 to about 1100 nm.

The SERS particle thus obtained may be subjected to further purification in order to isolate the SERS particle. The SERS particle may be purified by using dialysis in order to remove and exchange the reactants solvents/solutions with a buffer which is appropriate to storage or future applications.

There is also provided a particle prepared from the disclosed method. The particle comprises a metallic core having a plurality of Raman molecules extending from the surface of the metallic core and a biocompatible protective shell encapsulating the Raman molecules The particle may be a nanoparticle. The particle may be a microparticle.

The SERS signal intensity may be used as an indicator of surface roughness of the particle The particle may be stable for a period of time which is at least 1 week, at least 2 weeks, at least 3 weeks or at least 4 weeks.

Due to the quick encapsulation of the Raman molecules by the silica layer, the Raman molecules may not dissociate or leak from the particle. Hence, the SERS signal from the particle may be stable over a period of time of at least 1 week, at least 2 weeks, at least 3 weeks or at least 4 weeks.

The surface of the SERS particle may be coupled with functional groups or conjugated with an antibody, protein or polypeptide, depending on its future applications. The functionalized SERS particle may be used for multiplexed bioanalysis. The conjugated SERS particle may be used for in vitro or in vivo studies.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DESCRIPTION

Figure 1:
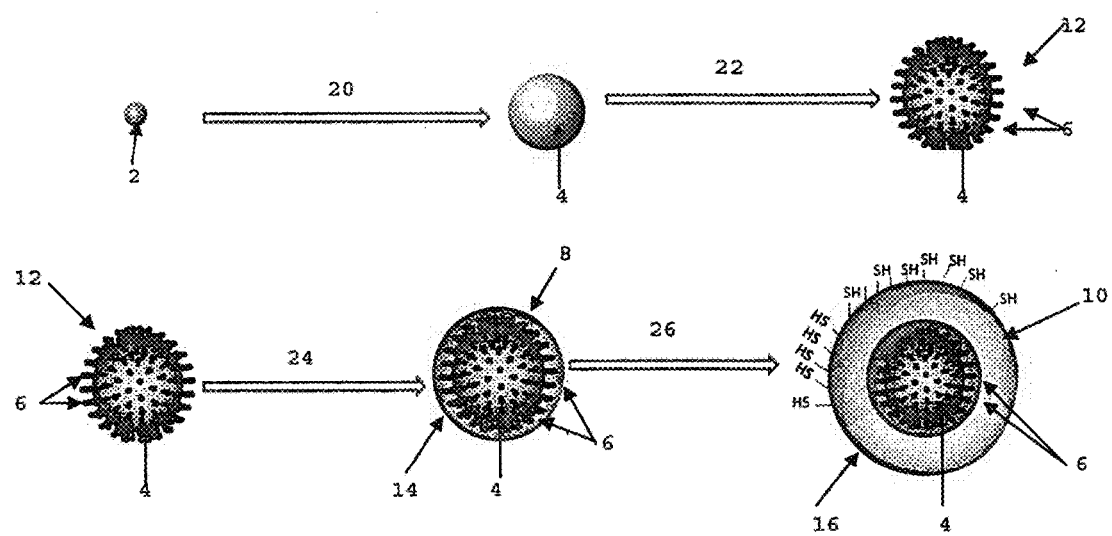
FIG. 1 is a schematic diagram showing the process to form a SERS particle according to one disclosed embodiment.

Referring to FIG. 1, there is shown a schematic diagram of a method 100 for preparing a SERS particle. In method 100, a metallic seed 2 was subjected to a growing step 20 to form a metallic core 4. The metallic core 4 was then subjected to an attaching step 22 and encapsulating step 24. In the attaching step 22, the metallic core 4 was mixed with the metallic core 4, Raman molecules and shell forming compounds to form a particle 12 having a plurality of Raman molecules 6 extending from the surface of the metallic core 4. At substantially the same moment, in the encapsulating step 24, a shell 8 encapsulates or forms around the Raman molecules 6 to form an encapsulated particle 14. The encapsulated particle 14 was then subjected to an increasing step 26 in order to thicken the thickness of the shell 8 to form the resultant particle 16 made up of a metallic core 4 having Raman molecules 6 extending from the surface of the metallic core 4 and a thickened shell 10 encapsulating the Raman molecules 6.

EXAMPLES

Non-limiting examples of the invention and comparative examples will be further described in greater detail by reference to specific Examples, which should not be construed as in any way limiting the scope of the invention.

All silane reagents were obtained from Gelest Inc. of Pennsylvania of the United States of America. All other chemicals were obtained from Sigma-Aldrich of Missouri of the United States of America.

Example 1

The process of FIG. 1 was used here. Metallic seeds 2 in the form of gold (Au) seed nanoparticles of 13 nm in sizes were subjected to a growing step 20 to form metallic core 4 particles in the form of 60 nm gold nanoparticles. In the growing step 20, 500 mL of 0.3 mM $HAuCl_4$ aqueous solution was heated to violent boiling within a short period of time (less than 20 min). To this boiling solution, 4.5 mL of pre-synthesized 13-nm Au seeds and 2 mL of 1 wt % sodium citrate solutions were injected within 4 seconds sequentially followed by 30 minutes boiling. To stabilize the resulting Au nanoparticles for silica coating and SERS tag optimization, various amounts of 5, 10, 15 or 20 mL of extra 1 wt % sodium citrate solution was injected into the freshly formed 60-nm Au nanoparticle solution. After boiling for one hour, the solution was cooled to room-temperature (RT or about 20° C. to about 25° C.) naturally under vigorous stirring. The as-stabilized 60 nm Au nanoparticles are labeled as 60-nm Au/0 mL citrate, 60-nm Au/5 mL citrate, 60-nm Au/10 mL citrate, 60-nm Au/15 mL citrate, and 60-nm Au/20 mL citrate, respectively.

The synthesized 60 nm Au nanoparticles were then subjected to attaching step 22 and encapsulating step 24 in which 500 mL of as-stabilized 60-nm Au nanoparticles in an Erlenmeyer flask were first mixed with 1 mL of 1 mM aminopropyltriethoxy silane (APTES) in an alcohol solution and then shaken for 15 minutes. Following this, 10 mL of freshly prepared 0.54 wt % sodium silicate solution (pH 10 to 11) and 5 mL of 100 µM CynamLA-381 the Raman molecules) aqueous solution were introduced into the mixture at room temperature and shaken for 15 minutes. The temperature of the shaker chamber was increased quickly from room temperature to 70° C. and the reaction mixture was shaken continuously for 8 hours at this temperature. To remove residual excess silicate and other small molecules, the as-synthesized SERS nanoparticles aqueous solution was transferred into a cellulose dialysis tubing for 48 hrs exhaustive dialysis, during which the container water was changed several times. At the end of dialysis, the as-purified 500 mL SERS nanoparticles solution was transferred and stored in either glass or plastic vessels prior to thickening or characterization, surface-functionalization and biomedical applications.

Figures 2A, 2B:
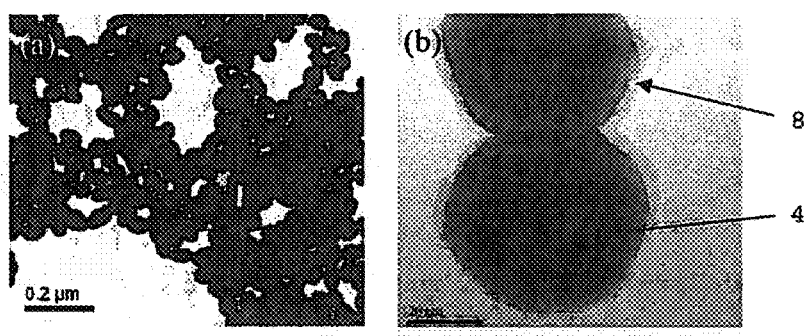
FIG. 2(a) is a transmission electron microscopy (TEM) image of nanoparticles having a thin silica shell made in accordance with Example 1 below. The scale bar of FIG. 2(a) is 0.2 µm.
FIG. 2(b) is another TEM image of the same nanoparticles as FIG. 2(a) but further magnified as compared to FIG. 2(a). The scale bar of FIG. 2(b) is 20 nm.

FIG. 2(a) is a TEM image of the Au/CynamLA-381@thin $SiO_2$ SERS nanoparticles (CynamLA-38 used as the Raman molecules) while FIG. 2(b) is a magnified image of FIG. 2(a). The thickness of the silica shell is about 2 to 5 nm.

Figure 3A:
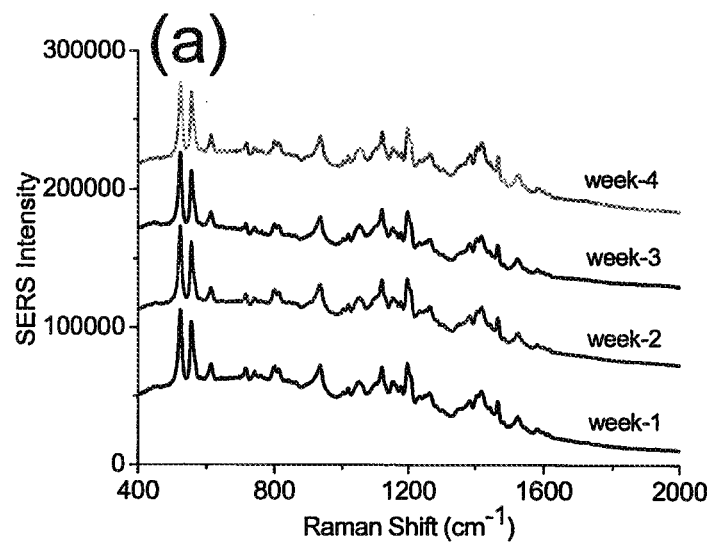
FIG. 3(a) is a graph showing the SERS intensity of the nanoparticles formed in accordance with Example 1 below when tested over a period of four weeks.
Figure 3B:
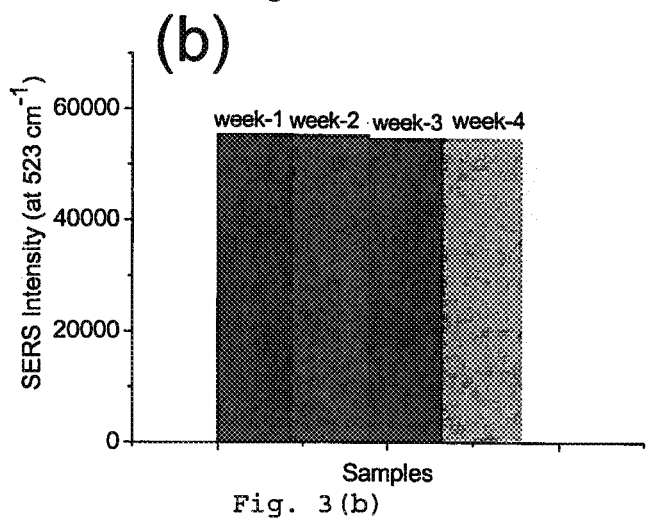
FIG. 3(b) is a bar graph showing the long term stability of the nanoparticles formed in accordance with Example 1 below.

FIG. 3(a) is a graph showing the SERS intensity of the Au/CynamLA-381@thin $SiO_2$ SERS nanoparticles over a period of four weeks. FIG. 3(b) is a bar graph showing the long term stability of the SERS intensity of the Au/CynamLA-381@thin $SiO_2$ SERS nanoparticles in which it can be observed that the SERS intensity of the nanoparticles was substantially unchanged over the test period of four week.

Example 2

The 500 mL as-purified thin since (less than 10 nm)-coated SERS nanoparticles aqueous solution was subjected to an increasing step 26 in which the nanoparticles aqueous solution was mixed with 1.25 mL of 3-mercaptopropyltrimethomysilane (MPTMS) and 2.5 mL of 26 wt % ammonia and then kept under constant shaking for 12 hours at room temperature (20° C. to about 25° C.). Desirable silica thickness can be obtained controlling the reaction time. Generally, the longer the reaction time, the thicker the silica shell until the MPTMS is consumed.

Purification was accomplished, by three-cycle centrifugation (at a RPM (rounds per minute) of 6,000 for 30-min) and re-dispersion (using fresh deionized water) process.

Figures 4A, 4B:
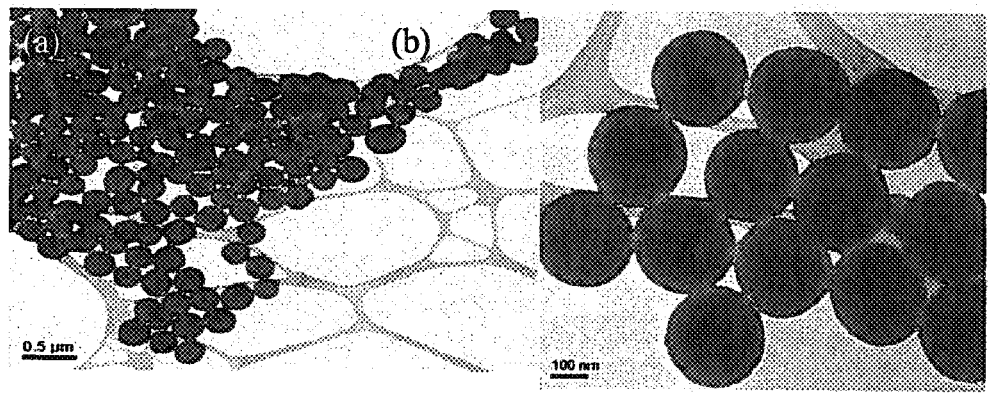
FIG. 4(a) is a TEM image of nanoparticles having a thickened silica shell made in accordance with Example 2 below. The scale bar of FIG. 4(a) is 0.5 µm.
FIG. 4(b) is another TEM image of the same nanoparticles as FIG. 4(a) but further magnified as compared to FIG. 4(a. The scale bar of FIG. 4(b) is 100 nm.
Figure 4C:
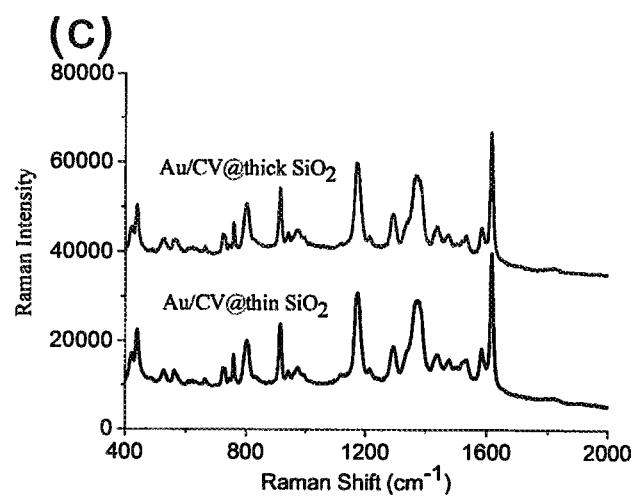
FIG. 4(c) is a graph showing the SERS intensity of the nanoparticles having a thin silica shell (about 2 to 5 nm) and a thickened silica shell (about 120 nm) FIG. 4(d) is a bar graph showing the SERS intensity of the same samples of FIG. 4(c).
Figure 4D:
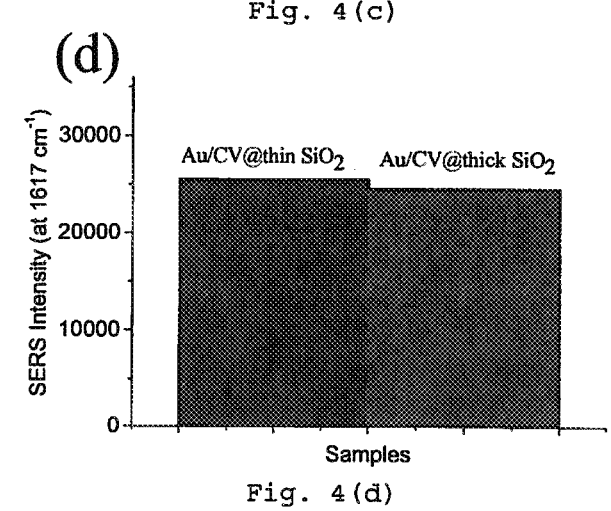

FIG. 4(a) is a TEM image of the nanoparticles with a thickened silica shell using crystal violet (CV) as the Raman molecule. The thickness of the thickened silica shell was about 120 nm. FIG. 4(c) is a graph showing the SERS intensity of the nanoparticles having a thin silica shell (about 2 to 5 nm) and a thickened silica shell (about 120 nm). FIG. 4(d) is a bar graph showing the SERS intensity of the same samples of FIG. 4(c). As can be observed, the thickness of the silica shell did not compromise the SERS signal.

Example 3

The Au/CynamLA-381@thin $SiO_2$ SERS nanoparticles were then subjected to surface-functionalization and bioconjugation.

To facilitate bio-conjugation, carboxylic acid (—COOH) functional groups were introduced on the Au/CynamLA-381@thin $SiO_2$ SERS nanoparticles by the following method. 2 mL as-purified thin silica coated SERS nanoparticles aqueous solution was mixed with 20 µL diluted 3-(triethoxysilyl)propylsuccinic anhydride isopropanol/water solution (0.5 mM). After shaking gently at room temperature for 12 hours, the COOH-modified SERS nanotags were obtained by three-cycle low round-per-minute (RPM) centrifugation and were stored in deionized water for further bio-conjugation uses. Further ScFv anti-HER2 conjugation follows the standard (1-Ethyl-3-[3-dimethylaminopropyl] carbodiimide hydrochloride)EDC/N-Hydroxysuccinimide (NHS) method. The EDC/NHS method is widely used to couple carboxyl groups to primary amines. Typically, EDC reacts with a carboxyl to form an amine-reactive O-acylisourea intermediate. In the presence of NHS, EDC can be used to convert carboxyl groups to amine-reactive NHS esters. This is accomplished by mixing the EDC with a carboxyl containing molecule and adding NHS. The excess EDC will undergo hydrolysis.

The ScFv anti-HER2 conjugated Au/CynamLA-381@thin $SiO_2$ SERS nanotags (or "ScFv anti-HER2 conjugated nanotags") were then tested in in vitro human breast cancer cell targeting. SKBR-3 cells are human breast cancer cells that produce HER2 receptors on the cell surface. Herein, ScFv anti-HER2 conjugated nanotags were used for SKBR-3 cells targeting/labeling. Cell culture was done as follows: briefly, the cell lines for HER2 positive (SKBR-3), and negative (MDA-MB231) were grown to the above-mentioned procedure in a 12-well plate. First, antibody conjugated silica-coated SERS nanotags were gently mixed with SKBR-3 live cells and incubated for 1 hour. Subsequently, the cells were harvested by gentle scraping after three-cycle of cold PBS buffer washing and re-suspended in 100 µL PBS. For control experiments, MDA-MB231 cells were treated with antibody-conjugated SEES nanotags, while SKBR-3 cells were incubated with silica-coated SERS nanotags to assess the non-specific binding. All SERS spectra were taken in cell suspensions based on cell density of $\sim 1 \times 10^6$ cells/mL. The resultant samples are labeled as "ScFv anti-HER2 conjugated nanotags in SKBR-3 cells" and "ScFv anti-HER2 conjugated nantags in MDA-MB231 cells".

The ScFv anti-HER2 conjugated nanotags have been successfully used for the recognition/targeting/labeling of HER2-positive SKBR-3 cells (FIG. 5) since SERS intensities have been observed for the various samples, This study successfully demonstrates the practical application of as-synthesized SERS nanotags for targeted detections of cancer cells.

Figure 5:
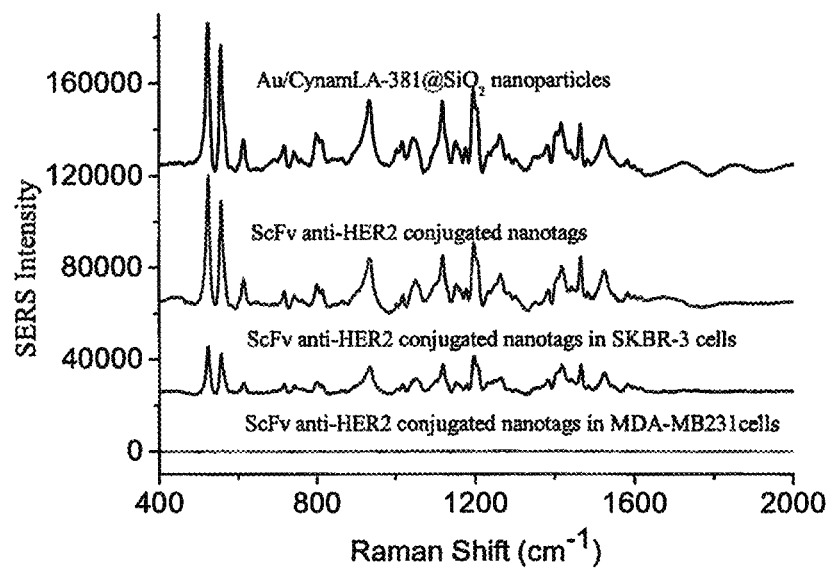
FIG. 5 is a graph showing the SERS intensity of four samples as used in Example 3 below.
Figures 6A, 6B:
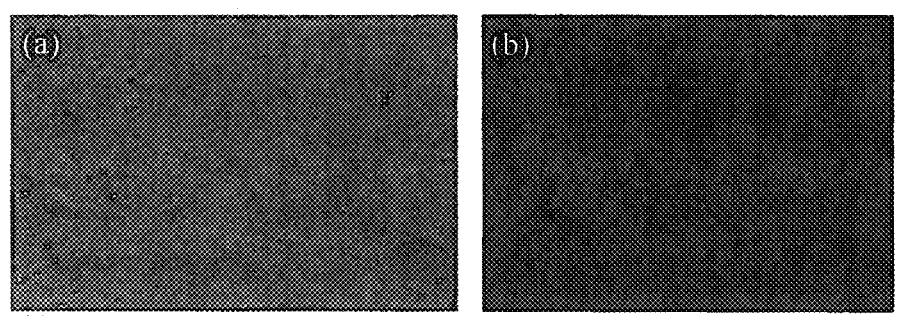
FIG. 6(a) is a fluorescence image of SEBR-3 cells recognized/targeted/labeled by FITC-attached ScFv anti-HER2 conjugated Au/CynamLA-381@SiO2 SERS nanotags.
FIG. 6(b) is a fluorescence image of MDA-MB231 cells incubated with the same FITC-attached SERS nanotags, according to Example 3 below.

Fluorescence image also confirmed the efficient recognition/targeting/labeling of HER2-positive SKBR-3 cells by the SERS nanotags (FIG. 6a); while the same SERS nanotags cannot recognize/target/label HER2 negative MDA-MB231 cells (FIG. 5 and FIG. 6b).

Example 4

The ScFv anti-HER2 conjugated nanotags were tested in in vivo tumor targeting. Balb/c nude mice from the Biological Resource Centre (Biomedical Sciences Institute) were anesthetized by intraperitoneal injection of ketamine (150 mg/kg)/xylazine (10 mg/kg) at the age of 4 to 6 weeks, and SKBR-3 or MDA-MB 231 cells were injected subcutaneously into the rear flank ($5 \times 10^6$ cells per site in a volume of 150 µL). When the tumors grew to a size around 0.2 cm in diameter, ScFv-conjugated thin silica-coated SERS nanotags (450 pM, 100 µL) were injected into the tail vein of the mice. After 5 hours, mice were anesthetized by intraperitoneal injection of ketamine and xylazine mixture solution and in vivo SERS measurements were performed using a Renishaw InVia Raman microscope with 785-nm laser excitation and 60 mW laser power. The integration time was set as 30 seconds and the laser was coupled to the sample through a 20× objective lens with a beam spot of approximately 2 mm. The animal experiment procedures were performed in accordance with a protocol approved by the Institutional Animal Care and Use Committee (IACUC).

Figure 7:
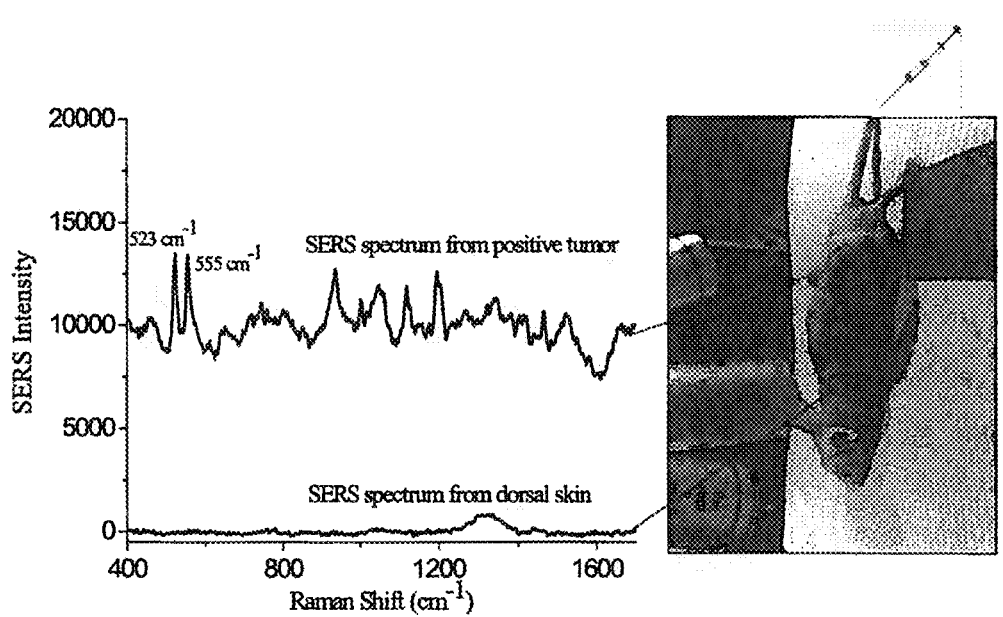
FIG. 7 shows the SERS intensities obtained from SKBR-3 xenograft mice. The samples tested are from the positive tumor and dorsal skin.

As seen from FIG. 7, ScFv anti-HER2 conjugated nanotags have also been successfully used for in-vivo tumor targeting. This result clearly demonstrates that ScFv anti-HER2 conjugated nanotags are able to specially detect/target HER2-positive tumor in-vivo.

Comparative Example 1

The SEPS-active silica-coated Au nanoparticles synthesized in aqueous solution was compared to those synthesized in alcohol solution (prior art).

First, the SERS-active silica-coated Au nanoparticles were synthesized in aqueous solution according to Example 1 at scaled-down amounts (1/100) using 5 mL 60 nm Au nanoparticles and 50 µL Raman molecule aqueous solution (100 µM) For comparison purpose, the SERS-active silica-coated Au nanoparticles were also synthesized in an alcohol solution via the Stöber method. Typically, 50 µL Raman molecule aqueous solution (100 µM) was added into 5 mL 60 nm Au nanoparticles. Hence, the ratio of Au nanoparticle to Raman molecules is the same for both processes. After shaking/mixing for 15 minutes, the mixture was transferred into 20 mL isopropanol and the pH value was adjusted to be 10 to 11 by adding 625 µL concentrated ammonia aqueous solution. In the subsequent 5 hours, a total tetraethyl orthosilicate (TEOS solution (10 mM, in isopropanol) of 0.6 mL was introduced at a time interval of 30 minutes. The coating was carried out under vigorous shaking for another 3 hours (8 hrs in total, same as that in aqueous solution synthesis) followed by same centrifugation/re-dispersion treatment as above.

The SERS-active silica-coated Au nanoparticles synthesized according to Example 1 above using crystal violet as the Raman molecules are labeled "Au/CV@SiO$_2$ prepared in aqueous solution". The SERS-active silica-coated Au nanoparticles synthesized according to the Stöber method are then labeled as "Au/CV@SiO$_2$@Stöber process".

Figure 8A:
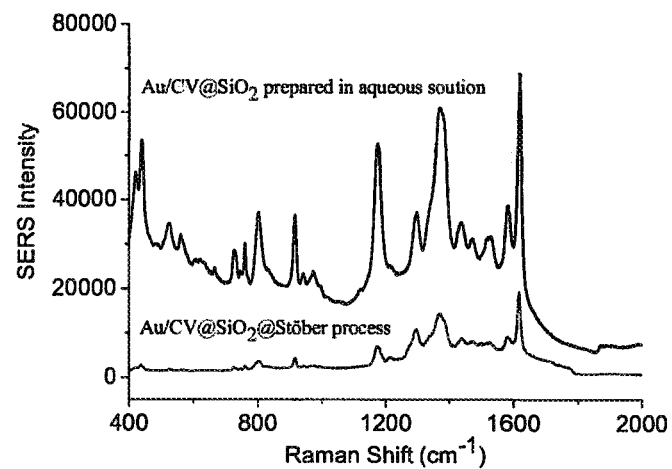
FIG. 8(a) is a graph showing the SERS intensities between a nanoparticle made in accordance with Example 1 when compared to another nanoparticle made in accordance with a prior art method (Stöber method) as discussed further in Comparative Example 1 below.
Figure 8B:
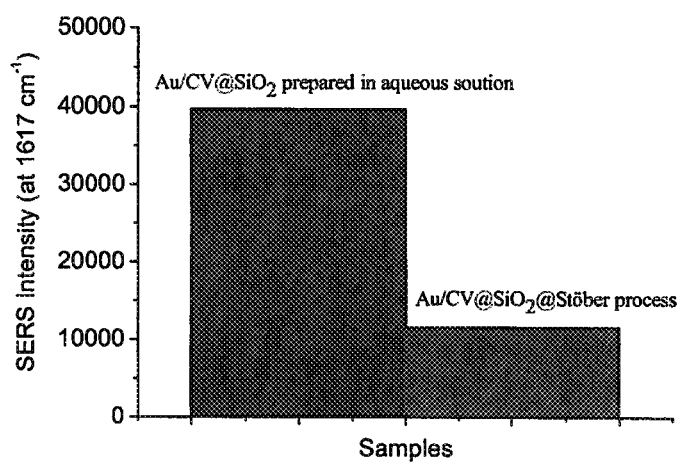
FIG. 8(b) is a bar graph based on the same samples investigated in FIG. 8(a).

As shown in FIG. 8(a) and FIG. 8(b), it can be observed that the use of an alcohol during the synthesis process has an adverse/detrimental effect on the SERS signals of the final SERS nanotags, even if the initial SERS signals are very strong. This could be due to the high solubilizing ability of the various alcohols (e.g. ethanol and isopropanol, the typical solvents for silica coating via Stöber process) for commonly used Raman molecules. As such, due to the presence of the alcohol, the Raman molecules may dissociate from the nanoparticles, leading to greatly reduced SERS signal intensity. In comparison, the SERS nanotags synthesized according to one disclosed embodiment have a strong SERS signal due to the strong adsorption of the Raman molecules on the surface of the core. The thickness of the silica shell for the sample "Au/CV@SiO$_2$ prepared in aqueous solution" is 4~6 nm (not shown); while the thickness of the silica shell for the sample "An/CV@SiO$_2$@Stöber process" is ~35 nm (not shown).

Comparative Example 2

The SERS-active silica-coated Au nanoparticles synthesized at an elevated temperature was compared to those synthesized at room temperature. The SERS-active silica-coated Au nanoparticles were as synthesized according to Example 1 above using crystal violet as the Raman molecules and labeled as "Au/CV@SiO$_2$ synthesized at 70° C. (8 hrs)".

As a comparison, instead of using an elevated temperature as shown in Example 1, the temperature was not increased but remained at room temperature (that is, a temperature of about 24° C.) for 48 hours to synthesize the nanotags, labeled as "Au/CV@SiO$_2$ synthesized at room temperature (48 hrs)".

Figure 9A:
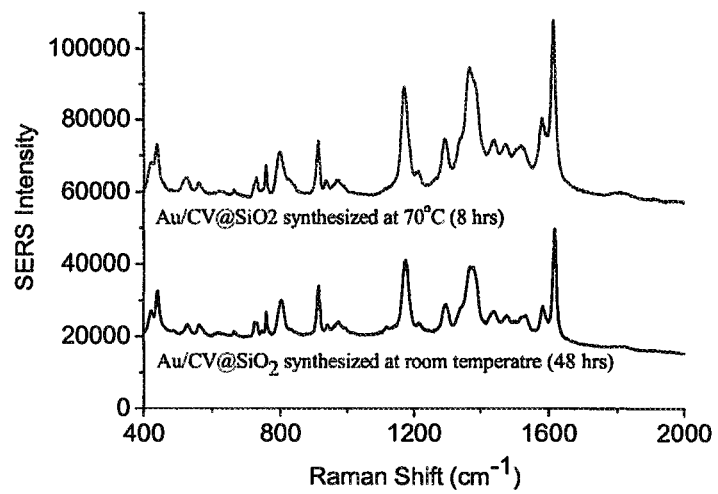
FIG. 9(a) is a graph snowing the SERS intensities between a nanoparticle made in accordance with Example 1 when compared to another nanoparticle made at a lower temperature as discussed further in Comparative Example 2 below.
Figure 9B:
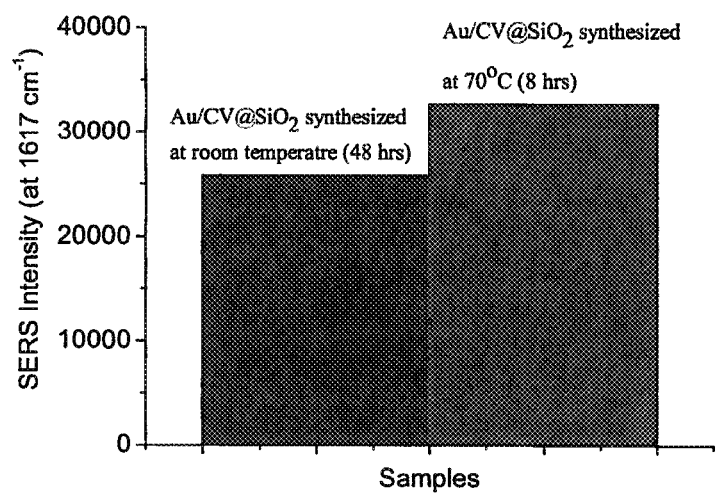
FIG. 9(b) is a bar graph based on the same samples investigated in FIG. 9(a).

As can be observed, the temperature increase not only shortens the synthesis time greatly (from 48 hours to 8 hours), but also enhances the SERS signal intensities (FIG. 9(a) and FIG. 3(b)). This is contributable to the faster and better encapsulation/protection of Raman molecules into the silica shells at elevated temperatures. Note: the silica shells are of the same thickness (4 to 6 nm) for above two oases.

Applications

The disclosed method may result in SERS particles with a strong SERS signal as compared to those made in accordance with the prior art. The Raman molecules may not dissociate easily from the SERS particles due to its quick encapsulation by the silica layer during the synthesis of such tags. The use of an aqueous solution during the thickening of the silica layer may also aid in enhancing the SERS intensity of the particles due to the strong adsorption of the Raman molecules on the surface of the core.

The disclosed method may synthesize the SERS particles for a shorter period of time as compared to prior art method. Hence, the disclosed method may reduce the time needed to encapsulate the Raman molecules by at least one-fold.

The SERS particles synthesized according to the disclosed method may be kept in an aqueous solution and be stable for a long period of time while retaining the SERS intensity. Hence, the SERS particles can be used for real-time in vivo imaging over a long period of time.

The SERS particles with a thickened silica layer may be used in any rigid environments including organic solvents without leaking of the Raman molecules into the environment. Advantageously, the as synthesized SERS particles can be used in diverse bio-applications.

The disclosed method can be used to synthesize SERS particles in which the Raman molecules are fluorescent dyes. The strong fluorescence of the fluorescent dyes can be quenched due to the strong or close adsorption of the dyes on the metallic core. This is not possible using the prior art (Stöber) method as the use of an alcoholic solution will cause any adsorbed Raman molecules to detach easily from the metallic core, leading to a substantial decrease or even no surface-adsorbed Raman molecules.

The disclosed method can be used with a variety of Raman molecules and need not be limited only to those Raman molecules that have certain functionalities. This is due to the fast encapsulation of the Raman molecules at the elevated temperature.

The disclosed method can be easily controlled and scaled up to produce a large quantity of SERS particles.

The SERS particles with various surface-functional groups may be used in multiplexed bioanalysis.

The SERS particles in the form of nanoparticles may be conjugated with various antibody, protein or polypeptide and used for in vitro or in vivo cell labeling, targeting or imaging.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A method of preparing a surface enhanced Raman spectroscopy (SERS) particle comprising attaching a plurality of Raman molecules on the surface of a metallic core while simultaneously encapsulating said core with a biocompatible protective shell at an elevated temperature, wherein said elevated temperature is selected to decrease the time taken for the simultaneous attachment and encapsulation more than one-fold relative to the same simultaneously attachment and encapsulation performed at 20° C.

2. The method as claimed in claim 1, wherein said simultaneous attaching and encapsulating comprises adding said metallic core to a solution comprising said Raman molecules, an organo coupling agent and a silica precursor under conditions to cause said Raman molecules to extend from the surface of said metallic core.

3. The method as claimed in claim 2, wherein said shell comprises silica.

4. The method as claimed in claim 2, wherein said organo coupling agent comprises amino functional groups and hydroxyl functional groups.

5. The method as claimed in claim 4, wherein said hydroxyl functional groups adsorbs said Raman molecules on the surface of said metallic core and cross-links with said silica precursor to form said silica shell.

6. The method as claimed in claim 1, wherein said elevated temperature is selected from the group consisting of 30° C. to 95° C., 30° C. to 40° C., 30° C. to 50° C., 30° C. to 60° C., 30° C. to 70° C., 30° C. to 80° C., 30° C. to 90° C., 40° C. to 95° C., 50° C. to 95° C., 60° C. to 95° C., 70° C. to 95° C., 80° C. to 95° C. and 90° C. to 95° C.

7. The method as claimed in claim 1, wherein the simultaneous attachment and encapsulation time is decreased at least two-fold, at least three-fold, at least four-fold, at least five-fold, at least six-fold, at least seven-fold, at least eight-fold, at least nine-fold, at least ten-fold, at least eleven-fold or at least twelve-fold, relative to the same simultaneous attachment and encapsulation performed at 20° C.

8. The method as claimed in claim 1, wherein said simultaneous attaching and encapsulating is undertaken for a period of time from 4 hours to 45 hours.

9. The method as claimed in claim 1, further comprising increasing the thickness of said biocompatible protective shell.

10. The method as claimed in claim 9, wherein said increasing comprises adding an aqueous solution of a coating precursor under alkaline conditions.

11. The method as claimed in claim 10, wherein said aqueous solution further comprises a catalyst selected from the group consisting of ammonia, 2-aminoethanethiol, ethanolamine, 2-(dimethylamino)ethanethiol, 2-(ethylthio)ethylamine and propylamine.

12. The method as claimed in claim 10, wherein said aqueous solution is substantially free of an alcohol.

13. The method as claimed in claim 10, wherein said coating precursor is selected from a silane compound.

14. The method as claimed in claim 10, wherein said alkaline conditions is selected from a pH in the range of 7 to 10.

15. The method as claimed in claim 10, wherein said increasing is undertaken for a period of time from at least 2 hours.

16. The method as claimed in claim 9, wherein the thickness of said biocompatible protective shell before said increasing is selected from 2 nm to 10 nm.

17. The method as claimed in claim 9, wherein the thickness of said biocompatible protective shell after said increasing is selected from 10 nm to 1100 nm.

18. The method as claimed in claim 1, wherein said metallic core comprises a transition metal.

19. The method as claimed in claim 1, wherein said metallic core has a cross-sectional diameter selected from 50 to 1000 nm.

20. The method as claimed in claim 1, wherein said Raman molecule is selected from the group consisting of a near infrared (NIR)-SERS active organic dye which belongs to the tricarbocyanine library (CyNAMLA), 4-(4-Aminophenylazo)phenylarsonic acid monosodium salt, arsenazo I, basic fuchsin, Chicago sky blue, direct red 81, disperse orange 3, HABA (2-(4-hydroxyphenylazo)-benzoic acid), erythrosin B, trypan blue, ponceau 3, ponceau SS, 3,3'-diethylthiatricarbocyanine, 1,5-difluoro-2,4-dinitrobenzene, cresyl violet, 2-naphthalenethiol, crystal violet, pyrazole, p-dimethylaminoazobenzene and mixtures thereof.

* * * * *